(12) United States Patent
Collin et al.

(10) Patent No.: US 7,883,690 B2
(45) Date of Patent: Feb. 8, 2011

(54) MASCARA COMPRISING A LIQUID FATTY PHASE AND A WAX

(75) Inventors: Nathali Collin, Sceaux (FR); Bertrand Piot, Paris (FR)

(73) Assignee: L'Oreal S.A., Paris (FR)

( * ) Notice: Subject to any disclaimer, the term of this patent is extended or adjusted under 35 U.S.C. 154(b) by 1223 days.

(21) Appl. No.: 10/415,138

(22) PCT Filed: Oct. 26, 2001

(86) PCT No.: PCT/FR01/03351

§ 371 (c)(1),
(2), (4) Date: Jul. 9, 2003

(87) PCT Pub. No.: WO02/34215

PCT Pub. Date: May 2, 2002

(65) Prior Publication Data

US 2004/0009201 A1    Jan. 15, 2004

(30) Foreign Application Priority Data

Oct. 27, 2000   (FR)   .................................. 00 13868

(51) Int. Cl.
*A61Q 1/10*      (2006.01)
(52) U.S. Cl. ...................... 424/70.7; 424/401
(58) Field of Classification Search .............. None
See application file for complete search history.

(56) References Cited

U.S. PATENT DOCUMENTS

| | | | |
|---|---|---|---|
| 5,849,278 A * | 12/1998 | Piot et al. | 424/70.7 |
| 5,858,338 A | 1/1999 | Piot et al. | |
| 5,911,974 A * | 6/1999 | Brieva et al. | 424/64 |
| 5,945,095 A | 8/1999 | Mougin et al. | |
| 6,066,316 A | 5/2000 | Shiojima et al. | |
| 6,156,804 A | 12/2000 | Chevalier et al. | |
| 6,227,735 B1 | 5/2001 | Gueret | |
| 6,464,967 B1 * | 10/2002 | Collin | 424/70.7 |
| 6,641,821 B1 * | 11/2003 | Collin et al. | 424/401 |
| RE38,362 E * | 12/2003 | Collin et al. | 424/63 |
| 6,946,123 B2 * | 9/2005 | De La Poterie et al. | 424/70.7 |

FOREIGN PATENT DOCUMENTS

| | | | |
|---|---|---|---|
| DE | 200 09 445 | | 9/2000 |
| EP | 005 922 | | 12/1979 |
| EP | 0 557 196 | | 8/1993 |
| EP | 557196 | * | 8/1993 |
| EP | 0 611 170 | | 8/1994 |
| EP | 0 749 746 | | 12/1996 |
| EP | 0 923 928 | | 6/1999 |
| FR | 2782918 | * | 3/2000 |
| FR | 2783707 | * | 3/2000 |
| JP | 6-9341 | | 1/1994 |
| JP | 9-30924 | | 2/1997 |
| JP | 10-324617 | | 12/1998 |
| JP | 11-171737 | | 6/1999 |
| JP | 11-263914 | | 9/1999 |
| JP | 11-263915 | | 9/1999 |
| JP | 11-279048 | | 10/1999 |
| WO | WO 91/12793 | | 9/1991 |

OTHER PUBLICATIONS

English language Derwent Abstract of DE 200 09 445, Sep. 21, 2000.
English language Derwent Abstract of EP 0 923 928, Jun. 23, 1999.
English language abstract of JP 9-30924, Feb. 4, 1997.
English Language esp@cenet abstract for JP 11-263914, Sep. 28, 1999.
English Language esp@cenet abstract for JP 11-263915, Sep. 28, 1999.

* cited by examiner

*Primary Examiner*—Jyothsna A Venkat
(74) *Attorney, Agent, or Firm*—Finnegan, Henderson, Farabow, Garrett & Dunner LLP

(57) ABSTRACT

The invention concerns a composition comprising, in a physiologically acceptable medium, at least a liquid fatty phase comprising at least a volatile organic solvent and at least an aqueous phase. The invention is characterised in that the aqueous phase contains a micro-dispersion of wax particles. The composition results, after being applied on keratinous fibres, in a water-resistant film and provides good curved shape to the keratinous fibres. The invention is applicable to mascara.

26 Claims, No Drawings

MASCARA COMPRISING A LIQUID FATTY PHASE AND A WAX

The subject of the present invention is a composition for coating keratinous fibres comprising a wax and a liquid fatty phase. The invention also relates to a method for coating keratinous fibres. The composition and the method according to the invention are more particularly intended for the eyelashes of human beings, but also for false eyelashes. The composition may be a make-up composition for the eyelashes also called a mascara, a make-up base for the eyelashes, a composition to be applied over a mascara, also called top coat, or a composition for the cosmetic treatment of the eyelashes. More especially, the invention relates to a mascara.

Generally, compositions for coating the eyelashes, called mascaras, comprise waxes for coating the eyelashes. These waxes may be dispersed in an aqueous medium, in particular using surfactants. However, the make-up film obtained with these compositions tends to crumble over time. The film which has thus been rendered fragile tends not to be resistant to rubbing, in particular of the fingers, and/or to water, during bathing or showers for example, which is incompatible with obtaining a make-up exhibiting good retention over time.

So-called waterproof mascaras are also known which comprise waxes in an anhydrous medium, in particular in a liquid fatty phase comprising organic solvents. These compositions may comprise, in addition, an aqueous phase dispersed in the liquid fatty phase, as the document WO-A-91/12793 describes for example. This document specifies, moreover, that the waterproofness of the mascara may be improved by adding to the aqueous phase a water-soluble film-forming polymer. However, with these mascaras, the eyelashes with applied make-up are only moderately thickened and the make-up obtained is a natural make-up with a moderate loading capacity. If it is desired to obtain a thick make-up on the eyelashes, that is to say to obtain a mascara with high loading capacity, it is necessary to incorporate a larger quantity of wax into the fatty phase. However, the increase in the amount of wax causes a rise in the viscosity of the mascara; the latter is very difficult to apply to the eyelashes. A mascara which is too viscous has a dry contact with the eyelashes, does not slip over the eyelashes and slows down the application of the brush over the eyelashes. These difficulties for the application of such a mascara do not allow proper deposition on the eyelashes and the make-up does not thicken the eyelashes.

The aim of the present invention is to avoid the disadvantages mentioned above and to make available a composition for coating keratinous fibres, in particular the eyelashes, which can be easily applied to the keratinous materials and which leads, after application, to a waterproof coat which thickens the keratinous fibres.

The Applicant has now observed, surprisingly, that such a coating of the keratinous fibres, in particular of the eyelashes, could be obtained using an aqueous microdispersion of particles of wax in a composition comprising an aqueous phase and a liquid fatty phase. A composition is then obtained which can be easily applied to the keratinous fibres and which forms a waterproof coat on the keratinous fibres. The make-up obtained thickens the keratinous fibres well: a make-up having a sufficiently high loading capacity is obtained. Moreover, the coat does not crumble and exhibits good resistance to rubbing, in particular to rubbing of the fingers. Furthermore, when the wax in the form of a wax microdispersion is a hard wax as defined below, the composition confers a satisfactory curling of the keratinous fibres and the curling obtained exhibits good retention over time: the curling of the eyelashes is maintained for at least 6 hours.

More precisely, the subject of the present invention is a composition comprising, in a physiologically acceptable medium, at least one liquid fatty phase comprising at least one volatile organic solvent, and at least one aqueous phase, characterized in that the aqueous phase contains a microdispersion of particles of wax.

Another subject of the invention is a mascara product comprising a reservoir containing a mascara composition as defined above, and provided with a system for applying the composition to the keratinous fibres, in particular the eyelashes.

The subject of the invention is also a method for coating the keratinous fibres, in particular the eyelashes, comprising the application, to the keratinous fibres, of a composition as defined above. The method for coating the keratinous fibres may be a method for the application of make-up to or the nontherapeutic cosmetic treatment of the keratinous fibres, in particular the eyelashes.

The subject of the invention is also the use of a composition as defined above for thickening the keratinous fibres, in particular the eyelashes, and/or for obtaining a high-load make-up application to the keratinous fibres.

The subject of the invention is also the use, in a composition comprising a physiologically acceptable medium, of an aqueous microdispersion of particles of wax, the wax having a hardness greater than or equal to 6 MPa, and a liquid fatty phase comprising at least one volatile organic solvent for thickening and/or curling the keratinous fibres, in particular the eyelashes.

The subject of the invention is also the use, in a composition comprising a physiologically acceptable medium, of an aqueous microdispersion of particles of wax, a liquid fatty phase comprising at least one volatile organic solvent and an additional wax present in the liquid fatty phase, for thickening the keratinous fibres, in particular the eyelashes and/or for obtaining a high-load make-up application to the keratinous fibres.

The subject of the invention is also the use, in a composition comprising a physiologically acceptable medium, of an aqueous microdispersion of particles of wax, the wax having a hardness greater than or equal to 6 MPa, a liquid fatty phase comprising at least one volatile organic solvent, and an additional wax present in the liquid fatty phase, for thickening and/or curling the keratinous fibres, in particular the eyelashes.

In the present application, the expression "composition for coating the keratinous fibres" is understood to mean a composition capable of forming a film on the keratinous fibres.

The expression physiologically acceptable should be understood to mean a medium compatible with the keratinous materials, such as a cosmetic medium.

a) The Wax Microdispersion:

The composition according to the invention comprises an aqueous microdispersion of particles of wax. The expression aqueous microdispersion of wax is understood to mean an aqueous dispersion of particles of wax in which the mean size of the said particles of wax is less than or equal to about 1 µm.

The expression "mean size of less than or equal to 1 µm" is understood to mean the size for which at least 50% by volume of the particles have a size of less than or equal to the mean size of 1 µm. The size of the particles of wax may be measured using a granulometer, for example the granulometer marketed under the reference Mastersizer 2000 by the company Malvern.

In the present application, a wax is a lipophilic compound which is solid at room temperature (25° C.), with a reversible change of solid/liquid state, having a melting point greater than or equal to 30° C., and which may be up to 120° C. By bringing the wax to the liquid state (melting), it is possible to make it miscible with oils and to form a microscopically homogeneous mixture; but on bringing the temperature of the mixture to room temperature, recrystallization of the wax in the oils of the mixture is obtained.

The melting point of the wax may be measured using a differential scanning calorimeter (DSC), for example the calorimeter sold under the name DSC 30 by the company METLER. A 15 mg sample of product placed in a crucible is subjected to a first rise in temperature ranging from 0° C. to 120° C., at the rate of heating of 10° C./minute, and is then cooled from 120° C. to 0° C. at a cooling rate of 10° C./minute and finally subjected to a second rise in temperature ranging from 0° C. to 120° C. at a heating rate of 5° C./minute. During the second rise in temperature, the variation of the difference in power absorbed by the empty crucible and by the crucible containing the sample of product is measured as a function of the temperature. The melting point of the compound is the value of the temperature corresponding to the summit of the peak of the curve representing the variation of the difference in power absorbed as a function of the temperature.

The wax microdispersions are dispersions of colloidal particles of wax, and are in particular described in "Microemulsions Theory and Practice", L. M. Prince Ed., Academic Press (1977) pages 21-32.

In particular, these wax microdispersions may be obtained by melting wax in the presence of a surfactant, and optionally of a portion of the water, and then gradually adding hot water with stirring. The intermediate formation of a water-in-oil type emulsion is observed followed by a phase inversion with final production of an oil-in-water type microemulsion. On cooling, a stable microdispersion of solid colloidal particles of wax is obtained. The wax microdispersions may also be obtained by stirring the mixture of wax, surfactant and water using stirring means such as ultrasound, a high-pressure homogenizer and turbines.

The particles of wax microdispersion preferably have mean sizes of less than 1 µm (in particular ranging from 0.02 µm to 1 µm), preferably of less than 0.5 µm (in particular ranging from 0.051 µm to 0.5 µm).

These particles essentially consist of a wax or a mixture of waxes. They may however comprise a minor proportion of oily and/or pasty fatty additives, a surfactant and/or a customary fat-soluble additive/active agent.

The waxes which can be used in the form of a microdispersion in the composition according to the invention are chosen from solid and rigid waxes at room temperature of animal, plant, mineral or synthetic origin and mixtures thereof. Preferably, the waxes may have a melting point greater than or equal to 45° C. approximately (in particular ranging from 45° C. to 120° C.), and in particular greater than or equal to 55° C. (in particular ranging from 55° C. to 120° C.), or even greater than or equal to 70° C. (in particular ranging from 70° C. to 120° C.). The wax may also have a hardness ranging from 0.05 MPa to 15 MPa. Advantageously, it is possible to use a wax (termed hard wax) having a hardness greater than or equal to 6 MPa, in particular ranging from 6 MPa to 30 MPa, and in particular ranging from 6 MPa to 15 MPa, to obtain a composition conferring a good curling on the keratinous fibres. Furthermore, the curling obtained exhibits good retention over time: the curling of the eyelashes is maintained for at least 6 hours.

The hardness is determined by measuring the compacting force measured at 20° C. using a texturometer sold under the name TA-TX2i by the company RHEO, equipped with a stainless steel cylinder having a diameter of 2 mm, moving at the measuring speed of 0.1 mm/s and penetrating into the wax at a penetration depth of 0.3 mm. To measure the hardness, the wax is melted at a temperature equal to the melting point of the wax+20° C. The molten wax is poured into a container having a diameter of 30 mm and a depth of 20 mm. The wax is recrystallized at room temperature (25° C.) for 24 hours, and then the wax is stored for at least 1 hour at 20° C. before carrying out the measurement of hardness. The value of the hardness is the measured compacting force divided by the surface of the texturometer cylinder in contact with the wax.

As wax having a hardness greater than or equal to 6 MPa (termed hard wax), there may be mentioned carnauba wax, microcrystalline wax, polyethylene waxes, Candelilla wax, hydrogenated jojoba oil, rice bran wax, Ozokerites, Chinese wax, Shellac wax, Ouricury wax.

As wax having a hardness of ranging less than 6 MPa (in particular less than or equal to 0.05 MPa and less than 6 MPa) (termed soft wax), there may be used beeswax, hydrogenated castor oil, lanolin wax, paraffin wax and Bayberry wax.

The composition according to the invention may preferably comprise from 0.1 to 50% by weight of dry matter of wax of the said wax microdispersion, in particular 1 to 30% by weight. It may also comprise a sufficient quantity of surfactant in order to make it possible to obtain a wax microdispersion, as well as a final composition, which is stable. In particular, it may comprise 0.01 to 30% by weight of customary surfactant, which may be chosen from the following compounds:

anionic surfactants, in particular optionally unsaturated fatty acid salts, having for example 12 to 18 carbon atoms; alkali metal salts or salts of organic bases with alkylsulphuric and alkylsulphonic acids having 12 to 18 carbon atoms or alkylarylsulphonic acids whose alkyl chain contains 6 to 18 carbon atoms; ether sulphates;

nonionic surfactants, in particular polyalkoxylated and/or polyglycerolated surfactants, and in particular fatty acids or fatty acid amides; fatty alcohols or alkylphenols; esters of fatty acids and polyols; alkanediols and alkyl ethers of alkanediols. There may also be mentioned alkyl carbamates of triglycerol, oxyethylenated or propoxylated derivatives of lanolin alcohols, lanolin fatty acids or mixtures thereof;

cationic surfactants, in particular quaternary ammonium derivatives.

The wax or mixture of waxes may be combined with one or more fatty (oily and/or pasty) additives. There may be mentioned in particular vegetable oils such as sunflower oil, jojoba oil; mineral oils such as paraffin oil; silicone oils; petroleum jelly; lanolin; fluorinated oils; hydrocarbon oils with a perfluorinated group; esters of fatty alcohols.

It is possible to introduce, in addition, into the microparticulate waxy phase fat-soluble active ingredients such as UV-screening agents, fat-soluble vitamins, fat-soluble cosmetic active agents.

b) The Liquid Fatty Phase:

The liquid fatty phase of the composition comprises at least one volatile organic solvent.

The expression "liquid fatty phase" in the present invention is understood to mean any nonaqueous medium which is liquid at room temperature and which is imiscible with water.

The expression "volatile organic solvent" is understood to mean an organic solvent capable of evaporating at room temperature from a support onto which it has been applied, in other words a solvent having a measurable vapour pressure at room temperature.

It is possible in particular to use one or more oils which are volatile at room temperature and atmospheric pressure having, for example, a vapour pressure, at ambient pressure and temperature >0 mmHg (0 Pa) and in particular ranging from $10^{-3}$ to 300 mmHg (0.13 Pa to 40,000 Pa), provided that the boiling point is greater than 30° C. These volatile oils facilitate, in particular, the application of the composition to the keratinous fibres. These oils may be hydrocarbon oils or silicone oils.

According to one embodiment of the invention, the volatile organic solvent may be a volatile hydrocarbon oil. The expression "hydrocarbon oil" is understood to mean an oil containing only hydrogen and carbon atoms.

The preferred volatile hydrocarbon oils which are suitable for the composition according to the invention are in particular isoparaffins, namely branched alkanes, comprising from 8 to 16 carbon atoms such as the "ISOPARs", PERMETYLs and in particular isododecane (also called 2,2,4,4,6-pentamethylheptane). It is of course also possible to use mixtures of such isoparaffins. Other volatile hydrocarbon oils such as petroleum distillates, in particular those sold under the name Shell Solt by the company SHELL, may also be used.

The volatile organic solvent may be present in the composition according to the invention in an amount ranging from 35% to 75% by weight, relative to the total weight of the composition, preferably from 45% to 70% by weight, and better still from 50% to 65% by weight.

As volatile organic solvents, there may also be used volatile silicones, such as for example cyclic and volatile silicone oils like octamethylcyclotetra-siloxane, decamethylcyclopentasiloxane, hexadecamethylcyclohexasiloxane, volatile linear silicones like octamethyltrisiloxane, heptamethylhexyltrisiloxane, heptamethyloctyltrisiloxane, or alternatively fluorinated volatile oils such as nonafluoromethoxybutane or perfluoromethylcyclopentane.

The liquid fatty phase may also contain nonvolatile oils, and in particular nonvolatile hydrocarbon and/or silicone and/or fluorinated oils.

As nonvolatile hydrocarbon oil, there may in particular be mentioned:

hydrocarbon oils of animal origin such as perhydrosqualene;

hydrocarbon oils of plant origin such as liquid triglycerides of fatty acids of 4 to 10 carbon atoms such as the triglycerides of heptanoic or octanoic acids, or sunflower, grapeseed, sesame, maize, apricot, castor, avocado, olive, cereal germ, soyabean, sweet almond, palm, rapeseed, cottonseed, hazelnut, macadamia or jojoba oils, triglycerides of caprylic/capric acids such as those sold by the company Stearineries Dubois or those sold under the names Miglyol 810, 812 and 818 by the company Dynamit Nobel, shea butter oil;

linear or branched hydrocarbons of mineral or synthetic origin such as petroleum jelly, polydecenes, hydrogenated polyisobutene such as parleam;

synthetic esters and ethers such as the oils of formula $R_{10}COOR_{11}$ in which $R_{10}$ represents the residue of a higher fatty acid comprising from 6 to 29 carbon atoms and $R_{11}$ represents a hydrocarbon chain containing from 3 to 30 carbon atoms, such as Purcellin oil, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate; the esters of polyols such as propylene glycol dioctanoate, neopentyl glycol diheptanoate, diethylene glycol diisonanoate and the pentaerythritol esters;

fatty alcohols which are liquid at room temperature containing a branched and/or unsaturated carbon chain having from 12 to 26 carbon atoms such as octyl dodecanol, oleyl alcohol, 2-hexyldecanol, 2-butyloctanol, 2-undecylpentadecanol;

higher fatty acids such as oleic acid, linoleic acid, linolenic acid;

and mixtures thereof.

The nonvolatile silicone oils which can be used in the composition according to the invention may be oils of low viscosity such as linear polysiloxanes whose degree of polymerization is preferably from 6 to 2000 approximately. There may be mentioned, for example, polydimethylsiloxanes (PDMS) having a viscosity greater than 10 mPa·s, phenyl dimethicones, phenyl trimethicones, polyphenylmethyl siloxanes and mixtures thereof.

The nonvolatile oils may be present in the composition according to the invention in an amount ranging from 0% to 5% by weight, relative to the total weight of the composition, preferably from 0% to 2% by weight. Advantageously, the composition according to the invention contains no nonvolatile oil, the composition thus making it possible to obtain a very good curling of the eyelashes.

Advantageously, the aqueous phase may be dispersed in the liquid fatty phase; the composition is then provided in the form of a water-in-oil or oil-in-water emulsion, and preferably in the form of a water-in-oil emulsion.

c) The Additives:

The composition according to the invention may contain, in the liquid fatty phase, at least one additional wax. This additional wax is not provided in the form of an aqueous microdispersion of particles of wax as defined above. The additional wax makes it possible to obtain a thick application of make-up to the eyelashes. The composition comprising the additional wax can therefore be used to thicken the keratinous fibres, in particular the eyelashes. This composition may also be used to curl the keratinous fibres, in particular the eyelashes, when the wax in microdispersion is a hard wax as defined above.

The additional wax can have a hardness ranging from 0.05 MPa to 15 MPa. It may be chosen from the waxes cited above (hard waxes and soft waxes).

The additional wax contained in the liquid fatty phase may be present in an amount ranging from 5% to 35% by weight, relative to the total weight of the composition, and preferably from 15% to 25% by weight.

The composition according to the invention may contain, in addition, in the liquid fatty phase, a lipophilic auxiliary film-forming polymer. This lipophilic auxiliary film-forming polymer may in particular be solubilized, or also termed fat-soluble, or dispersed, in particular in the presence of a stabilizer, in the liquid fatty phase. This lipophilic film-forming polymer confers in particular good retention of the coat after application of the composition to the keratinous fibres.

As lipophilic polymer, there may in particular be mentioned the copolymers resulting from the copolymerization of at least one vinyl ester and of at least one other monomer which may be an olefin, an alkyl vinyl ether or an allyl or methallyl ester, as described in application FR-A-22622303, whose content is incorporated into the present application by way of reference.

As lipophilic film-forming polymers which can be used in the invention, there may be mentioned polyalkylenes and in particular copolymers of $C_2$-$C_{20}$ alkenes, such as polybutene, alkyl celluloses with a saturated or unsaturated, linear or branched $C_1$ to $C_8$ alkyl radical such as ethyl cellulose and propyl cellulose, copolymers of vinylpyrrolidone (VP) and in particular the copolymers of vinylpyrrolidone and of $C_2$ to $C_{40}$ and even better $C_3$ to $C_{20}$ alkene. By way of example of a copolymer of VP which can be used in the invention, there may be mentioned the copolymer of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene, VP/acrylic acid/lauryl methacrylate.

Dispersions of film-forming polymer in the liquid fatty phase, in the presence of stabilizing agents, are in particular described in the documents EP-A-749746, EP-A-923928, EP-A-930060 whose content is incorporated by way of reference into the present application.

The lipophilic auxiliary film-forming polymer of the liquid fatty phase may be present in the composition in an amount ranging from 0.5% to 15% by weight, relative to the total weight of the composition, and even better from 2% to 10% by weight.

The composition according to the invention may comprise, in addition, a liquid fatty phase thickening agent. The thickening agent may be chosen from organomodified clays which are clays treated with compounds chosen in particular from quaternary amines and tertiary amines. As organomodified clays, there may be mentioned organomodified bentonites such as those sold under the name "Bentone 34" by the company RHEOX, organomodified hectorites such as those sold under the name "Bentone 27", "Bentone 38" by the company RHEOX. These clays are generally combined, in a known manner, with an activator such as propylene carbonate or ethanol in order to obtain the thickening of the liquid fatty phase.

The thickening agent may be present in an amount ranging from 0.5% to 15% by weight, relative to the total weight of the composition, and even better from 1% to 10% by weight.

In the composition according to the invention, the total weight of the liquid fatty phase may range from 65% to 99% by weight, relative to the total weight of the composition, and even better from 80% to 99% by weight.

The composition may also comprise at least one colouring matter such as pulverulent compounds and/or fat-soluble colourings, for example in an amount of 0.01 to 30% of the total weight of the composition. The pulverulent compounds may be chosen from the pigments and/or the pearlescent agents, other than those described above, which are normally used in cosmetic or dermatological compositions. Advantageously, the pulverulent compounds represent from 0.1 to 25% of the total weight of the composition and better still from 1 to 20%.

The pigments may be white or coloured, inorganic and/or organic. There may be mentioned, among inorganic pigments, titanium dioxide, optionally surface-treated, zirconium or cerium oxides, as well as iron or chromium oxides, manganese violet, ultramarine blue, chromium hydrate and ferric blue. Among the organic pigments there may be mentioned carbon black, pigments of the D & C type, and lacquers based on carmine, barium, strontium, calcium and aluminium.

The pearlescent pigments may be chosen from white pearlescent pigments such as mica coated with titanium, or with bismuth oxychloride, coloured pearlescent pigments such as mica-titanium with iron oxides, mica-titanium with in particular ferric blue or chromium oxide, mica-titanium with an organic pigment of the abovementioned type as well as pearlescent pigments based on bismuth oxychloride.

The composition according to the invention may also contain ingredients commonly used in cosmetics, such as plasticizers, fillers, preservatives, moisturizers, perfumes, vitamins, the alkalinizing or acidifying agents customarily used in the cosmetic field, and mixtures thereof.

Of course, persons skilled in the art would be careful to choose this or these optional additional compounds, and/or their quantity, so that the advantageous properties of the composition according to the invention are not, or not substantially, impaired by the addition envisaged.

The composition according to the invention may be prepared in a manner known to a person skilled in the art by first melting the additional waxes and by mixing the ingredients of the fatty phase, including the lipophilic additives. The pigments and the fillers, as well as the solvents thickened beforehand, are then added. The aqueous phase is then prepared by mixing the constituents, the aqueous microdispersion of wax is added and the entire aqueous phase is dispersed in the fatty phase.

The composition according to the invention is intended for a mascara product comprising a reservoir, containing the said mascara composition, and a system for applying the said composition to the keratinous fibres, in particular the eyelashes. The reservoir is provided, in a known manner, with an opening in which a draining system is lodged. The application system comprises a wand provided at a first end with a brush and at a second end with a cap intended to close the reservoir. Such a packaging is in particular illustrated in FIG. 7 of application EP-A-611170 which is incorporated by way of reference.

The invention is illustrated in greater detail in the following examples.

EXAMPLE 1

A microdispersion of carnauba wax having the following composition was prepared:

| | | |
|---|---|---|
| Carnauba wax | | 30 g |
| Polyoxyethylenated (30 EO) glyceryl monostearate (TAGAT S from GOLDSCHMIDT) | | 7.5 g |
| Preservatives | | 0.5 g |
| Water | qs | 100 g |

The wax, the surfactant and the preservative were heated to 95° C. while homogenizing the mixture, with moderate stirring. Water, heated to 95° C., was then incorporated while continuing to stir. The mixture was cooled to room temperature in order to obtain a wax microdispersion having a mean particle diameter of about 170 nm.

EXAMPLE 2

A mascara having the following composition was prepared:

| | | |
|---|---|---|
| Wax microdispersion of Example 1 | | 6.6 g |
| Carnauba wax | | 5.4 g |
| Rice bran wax | | 2.55 g |
| Paraffin | | 2.5 g |
| Beeswax | | 9.55 g |
| Bentonite | | 5.4 g |
| Propylene carbonate | | 1.7 g |
| Ethyl alcohol | | 0.7 g |
| Vinyl acetate/allyl stearate (65/35) copolymer (Mexomère PQ from CHIMEX) | | 7.2 g |
| Polyvinyl laurate (Mexomère PP from CHIMEX) | | 0.75 g |
| D-panthenol | | 0.2 g |
| Talc | | 0.98 g |
| Pigments | | 4.8 g |
| Preservatives | qs | |
| Isododecane | qs | 100 g |

This mascara can be easily applied to the eyelashes and makes it possible to obtain a make-up which is waterproof and which thickens the eyelashes. Good curling of the eyelashes is also obtained which is maintained for at least six hours.

The invention claimed is:

1. A mascara composition comprising, in a physiologically acceptable medium, at least one liquid fatty phase comprising 45% to 75% by weight relative to the total weight of the composition of at least one volatile organic solvent and at least one aqueous phase comprising a microdispersion of particles of at least one wax;
   wherein the at least one aqueous phase is dispersed within the liquid fatty phase such that the liquid fatty phase is continuous;
   wherein the at least one liquid fatty phase further comprises at least one additional wax present in an amount ranging from about 15% to about 25% by weight, relative to the total weight of the composition,
   wherein the at least one wax has a hardness ranging from about 6 MPa to about 15 MPa, and
   wherein the at least one additional wax has a hardness ranging from greater than or equal to about 0.05 MPa to less than about 6 MPa.

2. The mascara composition according to claim 1, wherein the microdispersion of the at least one wax comprises particles of the at least one wax having a mean size of less than about 1 μm.

3. The mascara composition according to claim 2, wherein the microdispersion of the at least one wax comprises particles of the at least one wax having a mean size of less than about 0.5 μm.

4. The mascara composition according to claim 1, wherein the at least one wax is chosen from waxes having a melting point ranging from about 30° C. to about 120° C.

5. The mascara composition according to claim 1, wherein the at least one wax is chosen from carnauba wax, microcrystalline wax, polyethylene waxes, Candelilla wax, hydrogenated jojoba oil, rice bran wax, Ozokerites, Chinese wax, Shellac wax, and Ouricury wax.

6. The mascara composition according to claim 1, wherein the at least one wax of the microdispersion is present in a dry matter content ranging from about 0.1% to about 50% by weight, relative to the total weight of the composition.

7. The mascara composition according to claim 6, wherein the at least one wax of the microdispersion is present in a dry matter content ranging from about 1% to about 30% by weight, relative to the total weight of the composition.

8. The mascara composition according to claim 1, wherein the microdispersion of the particles of the at least one wax further comprise at least one additive chosen from oily fatty additives, pasty fatty additives, fat-soluble additives, and fat-soluble active agents.

9. The mascara composition according to claim 1, further comprising at least one surfactant.

10. The mascara composition according to claim 1, wherein the at least one volatile organic solvent is chosen from volatile hydrocarbon oils.

11. The mascara composition according to claim 1, wherein the at least one volatile organic solvent is chosen from isoparaffins comprising from 8 to 16 carbon atoms.

12. The mascara composition according to claim 1, wherein the at least one volatile organic solvent is present in an amount ranging from about 50% to about 65% by weight, relative to the total weight of the composition.

13. The mascara composition according to claim 1, wherein the at least one continuous liquid fatty phase further comprises at least one lipophilic auxiliary film-forming polymer.

14. The mascara composition according to claim 13, wherein the at least one lipophilic auxiliary film-forming polymer is present in an amount ranging from about 0.5% to about 15% by weight, relative to the total weight of the composition.

15. The mascara composition according to claim 1, further comprising at least one additional film-forming polymer solubilized or dispersed in the at least one aqueous phase.

16. The mascara composition according to claim 1, wherein the at least one additional wax is chosen from beeswax, hydrogenated castor oil, lanolin wax, paraffin wax and Bayberry wax.

17. The mascara composition according to claim 1, wherein the composition is in the form of a water-in-oil emulsion.

18. The mascara composition according to claim 1, further comprising at least one additive chosen from thickeners, plasticizers, fillers, colouring matters, preservatives, moisturizers, perfumes, vitamins, alkalinizing agents, and acidifying agents.

19. A mascara product comprising
   a reservoir, wherein the reservoir comprises a mascara composition comprising, in a physiologically acceptable medium, at least one liquid fatty phase comprising 45% to 75% by weight relative to the total weight of the composition of at least one volatile organic solvent and at least one aqueous phase comprising a microdispersion of particles of at least one wax;
   wherein the at least one aqueous phase is dispersed within the liquid fatty phase such that the liquid fatty phase is continuous;
   wherein the at least one liquid fatty phase further comprises at least one additional wax present in an amount ranging from about 15% to about 25% by weight, relative to the total weight of the composition;
   wherein the at least one wax has a hardness ranging from about 6 MPa to about 15 MPa, and
   wherein the at least one additional wax has a hardness ranging from greater than or equal to about 0.05 MPa to less than about 6 MPa, and
   a system for applying said composition to keratinous fibres.

20. A process for coating keratinous fibres comprising
   applying to the keratinous fibres a mascara composition comprising, in a physiologically acceptable medium, at least one liquid fatty phase comprising 45% to 75% by weight relative to the total weight of the composition of at least one volatile organic solvent and at least one aqueous phase comprising a microdispersion of particles of at least one wax;
   wherein the at least one aqueous phase is dispersed within the liquid fatty phase such that the liquid fatty phase is continuous;
   wherein the at least one liquid fatty phase further comprises at least one additional wax present in an amount ranging from about 15% to about 25% by weight, relative to the total weight of the composition;
   wherein the at least one wax has a hardness ranging from about 6 MPa to about 15 MPa; and
   wherein the at least one additional wax has a hardness ranging from greater than or equal to about 0.05 MPa to less than about 6 MPa.

21. A process for making up and/or for non-therapeutic treating of keratinous fibres comprising
   applying to said keratinous fibres a mascara composition comprising, in a physiologically acceptable medium, at least one liquid fatty phase comprising 45% to 75% by weight relative to the total weight of the composition of at least volatile organic solvent and at least one aqueous phase comprising a microdispersion of particles of at least one wax;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

22. A process for curling keratinous fibres comprising applying to said keratinous fibres a mascara composition comprising, in a physiologically acceptable medium, at least one liquid fatty phase comprising 45% to 75% by weight relative to the total weight of the composition of at least one volatile organic solvent and at least one aqueous phase comprising a microdispersion of particles of at least one wax;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

23. A process for thickening keratinous fibres and/or for obtaining a high-load make-up application to keratinous fibres comprising applying to said keratin fibres a mascara composition comprising, in a physiologically acceptable medium, at least one liquid fatty phase comprising 45% to 75% by weight relative to the total weight of the composition of at least one volatile organic solvent and at least one aqueous phase comprising a microdispersion of particles of at least one wax;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

24. A process for thickening and/or curling keratinous fibres comprising applying to the keratinous fibres a mascara composition comprising, in a physiologically acceptable medium, an aqueous microdispersion of particles of at least one wax, wherein the at least one wax has a hardness greater than or equal to about 6 MPa, and at least one liquid fatty phase comprising 45% to 75% by weight relative to the total weight of the composition of at least one volatile organic solvent;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

25. A process for thickening keratinous fibres comprising applying to the keratinous fibres a mascara composition comprising, in a physiologically acceptable medium, an aqueous microdispersion of particles of at least one wax, at least one liquid fatty phase comprising 45% to 75% by weight relative to the total weight of the composition of at least one volatile organic solvent, and at least one additional wax present in the at least one liquid fatty phase;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

26. A process for thickening and/or curling the keratinous fibres comprising applying to the keratinous fibres a mascara composition comprising, in a physiologically acceptable medium, an aqueous microdispersion of particles of at least one wax, wherein the at least one wax has a hardness greater than or equal to about 6 MPa, at least one liquid fatty phase comprising 45% to 75% by weight relative to the total weight of the composition of at least one volatile organic solvent, and at least one additional wax present in the at least one liquid fatty phase;

wherein the at least one aqueous phase is dispersed within the liquid fatty phase such that the liquid fatty phase is continuous;

wherein the at least one liquid fatty phase further comprises at least one additional wax present in an amount ranging from about 15% to about 25% by weight, relative to the total weight of the composition;

wherein the at least one wax has a hardness ranging from about 6 MPa to about 15 MPa; and wherein the at least one additional wax has a hardness ranging from greater than or equal to about 0.05 MPa to less than about 6 MPa.

* * * * *

UNITED STATES PATENT AND TRADEMARK OFFICE
CERTIFICATE OF CORRECTION

| | | |
|---|---|---|
| PATENT NO. | : 7,883,690 B2 | Page 1 of 1 |
| APPLICATION NO. | : 10/415138 | |
| DATED | : February 8, 2011 | |
| INVENTOR(S) | : Nathalie Collin and Bertrand Piot | |

It is certified that error appears in the above-identified patent and that said Letters Patent is hereby corrected as shown below:

Title page, item (75), after "Inventors:",
"Nathali Collin, Sceaux (FR)" should read --Nathalie Collin, Sceaux (FR)--.

Signed and Sealed this
Twenty-sixth Day of April, 2011

David J. Kappos
*Director of the United States Patent and Trademark Office*